United States Patent [19]

Jain et al.

[11] Patent Number: 5,688,829
[45] Date of Patent: Nov. 18, 1997

[54] THERAPEUTIC INJECTABLE ANALGESIC COMPOSITION CONTAINING NIMESULIDE AND A PROCESS FOR THE MANUFACTURE THEREOF

[75] Inventors: Rajesh Jain; Amarjit Singh, both of New Delhi, India

[73] Assignee: Panacea Biotec Limited, New Delhi, India

[21] Appl. No.: 662,704

[22] Filed: Jun. 13, 1996

[30] Foreign Application Priority Data

| Jul. 25, 1995 | [IN] | India | 1389/DEL/95 |
| Nov. 6, 1995 | [IN] | India | 2046/DEL/95 |
| Nov. 8, 1995 | [IN] | India | 2047/DEL/95 |
| Nov. 8, 1995 | [IN] | India | 2048/DEL/95 |

[51] Int. Cl.$^6$ .................................................. A61K 31/18
[52] U.S. Cl. .................................................. 514/605
[58] Field of Search .................................................. 514/605

[56] References Cited

U.S. PATENT DOCUMENTS 5,283,261  2/1994  Drago .................................................. 514/605

Primary Examiner—William R. A. Jarvis
Attorney, Agent, or Firm—Ladas & Parry

[57] ABSTRACT

Therapeutic injectable analgesic pharmaceutical compositions for intramuscular administration containing nimesulide. The pharmaceutical compositions comprise nimesulide, dimethylacetamide, benzyl benzoate and ethyl oleate.

16 Claims, No Drawings

THERAPEUTIC INJECTABLE ANALGESIC COMPOSITION CONTAINING NIMESULIDE AND A PROCESS FOR THE MANUFACTURE THEREOF

The present invention relates to a novel therapeutic injectable analgesic pharmaceutical composition containing nimesulide which is N-(4-nitro, 2-phenoxyphenyl) methanesulfonamide, for intra-muscular administration and a process for the manufacture thereof.

BACKGROUND OF THE INVENTION

The use of nimesulide through intra-muscular administration as an analgesic agent has not been successful because Nimesulide is practically insoluble in water and its formulations in conventional oily bases or as suspensions result in depot formation in the muscular tissues which defies the main objective of quick relief.

The market and literature survey shows that no parenteral dosage form of Nimesulide is reported. (Drugs, 48 (3) 431–454, 1994).

An injectable formulation of nimesulide has been reported in the prior art (PCT Patent No. WO 95/34533) which utilizes a salt form of nimesulide (nimesulide-L-lysine) complexed with cyclodextrins. The maximum solubility achieved was reported to be 2.4 mg/mL, which is not suitable for an intramuscular injection as it would require very large volumes to administer therapeutic doses. The reported oral dose of nimesulide ranges between 100 to 400 mg per day. Contemplating that the intramuscular dose is half of the oral dose, 50 mg of the drug needs to be injected which would require approximately 20 ml of the solution described in the prior art. See WO 95/34533.

In the present invention we report an intramuscular injection formulation of nimesulide which incorporates the parent drug molecule in a suitable base having a concentration of 50mg/ml. With this formulation therapeutically effective doses of nimesulide can be administered conveniently. Moreover, the present invention gives the flexibility of injecting 0.5 ml to 3.0 ml of the 50 mg/ml solution as per the dosage requirements.

The present invention utilizes solubilization techniques to achieve such high concentrations of nimesulide and no salt forms or complexing agents were used as reported previously.

It is an object of the present invention to provide a novel therapeutic injectable analgesic composition containing nimesulide for intra-muscular administration from which the nimesulide is rapidly absorbed and distributed in body fluids.

It is a further object of the present invention to provide a process for the preparation of the novel therapeutic injectable analgesic composition containing nimesulide, according to the present invention, for intra-muscular administration.

SUMMARY OF THE INVENTION

The present invention provides a novel therapeutic injectable analgesic pharmaceutical composition for intramuscular administration which composition comprises:

| | |
|---|---|
| Nimesulide | 2.5% to 10% w/v and |
| Parenteral absorption enhancing vehicle base | 90% to 97.5% w/v. |

The said parenteral absorption enhancing vehicle base comprises

| | |
|---|---|
| Dimethylacetamide | 5% to 12% w/v, |
| Benzyl benzoate | 20% to 50% w/v, |
| Benzyl alcohol | 0% to 10% w/v, and |
| Ethyl oleate | 30% to 65% w/v. |

According to a preferred embodiment of the present invention, the novel therapeutic injectable analgesic composition comprises:

| | |
|---|---|
| Nimesulide | 5% w/v, |
| Dimethylacetamide | 10% w/v, |
| Benzyl benzoate | 40% w/v, |
| Benzyl alcohol | 2% w/v, and |
| Ethyl oleate | 30% to 65% w/v. |

DETAILED DESCRIPTION OF THE INVENTION

The present invention provides a novel therapeutic injectable analgesic pharmaceutical composition for intramuscular administration which composition comprises:

| | |
|---|---|
| Nimesulide | 2.5% to 10% w/v and |
| Parenteral absorption enhancing vehicle base | 90% to 97.5% w/v. |

The said parenteral absorption enhancing vehicle base comprises

| | |
|---|---|
| Dimethylacetamide | 5% to 12% w/v, |
| Benzyl benzoate | 20% to 50% w/v, |
| Benzyl alcohol | 0% to 10% w/v, and |
| Ethyl oleate | 30% to 65% w/v. |

According to a preferred embodiment of the present invention, the novel therapeutic injectable analgesic composition comprises:

| | |
|---|---|
| Nimesulide | 5% w/v, |
| Dimethylacetamide | 10% w/v, |
| Benzyl benzoate | 40% w/v, |
| Benzyl alcohol | 2% w/v, and |
| Ethyl oleate | 30% to 65% w/v. |

According to another preferred embodiment of the present invention, the Benzyl benzoate used is replaced in part by 5% to 10% w/v of CREMOPHOR EL (trademark) (poly oxyethylene glycolated castor oils)

If part of benzyl benzoate is replaced with 5% to 10% w/v of Cremophor EL then the amount of benzyl benzoate used in the preferred embodiment is 30 to 35% w/v.

According to another preferred embodiment of the present invention, a conventionally known anti-oxidant such as ascorbyl palmirate, butyl hydroxy anisole, butyl hydroxy toluene, propyl gallate and a-tocopherol is added to the injectable analgesic composition.

The present invention also provides a process for the preparation of the novel therapeutic injectable analgesic composition, according to the present invention, which process comprises the following steps:

(a) 5% to 12% w/v of Dimethylacetamide and 20% to 50% w/v of Benzyl benzoate are mixed in a container fitted with a Stirrer at slow speed (1000–1500 rpm) and to that 3% to 7% w/v of Nimesulide is added and stirred till completely dissolved, (b) 0% to 10% w/v of Benzyl alcohol and a portion of 30% to 65% w/v of Ethyl oleate are mixed in a container fitted with a stirrer, (c) the mixture obtained in step (a) is added to the mixture obtained in step (b) under slow stirring and the volume of the mixture obtained is made up to 100 ml by the rest of the amount of ethyl oleate resulting in the preparation of the desired injectable analgesic Composition.

The amount of ethyl oleate in the preferred embodiment is in a range due to ethyl oleate being added in step (c) to bring the total volume up to 100 ml.

According to a preferred embodiment of the Process according to the present invention, in the step (a) of the process 10% w/v of Dimethylacetamide and 40% w/v of Benzyl benzoate are mixed and to that 5% w/v of Nimesulide is added. In the step (b) of the process, 2% w/v of Benzyl alcohol and a portion of 30% to 65% w/v of Ethyl oleate are mixed.

Preferably step (c) of the process is carried out under continuous nitrogen flushing and the resulting solution obtained is passed through 0.22 u nylon membrane filter.

According to another preferred embodiment, of the present invention, a conventionally known anti-oxidant such as ascorbyl palmirate, butyl hydroxy anisole, butyl hydroxy toluene, propyl galate and octocophenol is added to the said injectable analgesic composition. The anti-oxidant can be added at any step of the process.

The present invention is exemplified by the following examples for the preparation of the injectable analgesic composition.

EXAMPLE 1

(a) Mix 10 g of Dimethylacetamide and 40 g of Benzyl benzoate in a container fitted with a stirrer at slow speed (1000–1200 rpm) at a temperature between 25°–30° C. Add 5 g of Nimesulide in small increments and stir until completely dissolved.

(b) Mix 10 g of Cremophor EL and an amount of Ethyl oleate in a container fitted with a stirrer at room temperature.

(c) Add the mixture obtained in step (a) to the mixture obtained in step (b) under slow stirring and stir for about 30 minutes. Make the volume up to 100 ml with Ethyl oleate and filter through 0.22 u nylon membrane filter to make it sterile.

EXAMPLE II (a) Mix 20 g of Dimethylacetmide and 76 g of Benzyl benzoate in a container fitted with a stirrer at slow speed at a temperature between 25°–30° C. Add to the mixture obtained 10 g of Nimesulide in small amounts at a time and stir until completely dissolved.

(b) Mix 4 g of Benzyl alcohol and an amount of Ethyl oleate in a container fitted with a stirrer at room temperature.

(c) Add the mixture obtained in step (a) to the mixture obtained in step (b) under slow stirring and stir for about 30 minutes. Make up the volume up to 200 ml with Ethyl oleate and filter through 0.22 u nylon membrane filter to make it sterile.

The injectable analgesic composition, according to the present invention, on preliminary animal and preclinical trials has shown to possess marked analgesic activity. Further it has been found to be non-toxic even on repeated applications on the same site. No incidence of tissue necrosis or any other side effect was observed. The analgesic dose ranges from 0.16 mg/kg to 8.4 mg/kg. This analgesic composition is very effective and useful for the treatment of acute painful conditions like-post operative trauma, pain associated with cancer, sports injuries and the like.

The analgesic activity of the therapeutic composition, prepared according to the present invention, was found to be dose dependent and passed the tests of subacute toxicity and undue toxicity.

The preclinical toxicology studies showed values at $LD_{50}=129.5$ mg/kg, $ED_{50}=3$ mg/kg with therapeutic index= 43.13 in mice. This demonstrates the high safety of the present invention.

The therapeutic injectable analgesic composition, according to the present invention, is not a mere admixture but has properties different from the sum total of the properties of its ingredients, as stated herein above.

Since many apparently different embodiments of the present invention could be made without departing from the spirit and scope thereof, it is intended that the description of the invention herein be interpreted as being illustrated only and not limiting in any manner whatsoever.

We claim:

1. A therapeutic injectable analgesic pharmaceutical composition for intra-muscular administration comprising:

| Nimesulide | 2.5% to 10% w/v and |
| Parenteral absorption enhancing vehicle base | 90% to 97.5% w/v | wherein said parenteral absorption enhancing base comprises;

| Dimethylacetamide | 5% to 12% w/w, |
| Benzyl benzoate | 20% to 50% w/v and |
| Ethyl oleate | 30% to 65% w/v. |

2. The pharmaceutical injectable composition as claimed in claim 1 further comprising up to 10% w/v benzyl alcohol.

3. A pharmaceutical injectable composition as claimed in claim 2 wherein said parenteral absorption enhancing base comprises:

| Dimethylacetamide | 10% w/v |
| Benzyl benzoate | 40% w/v |
| Benzyl alcohol | 2% w/v and |
| Ethyl oleate | 30% to 65% w/v. |

4. A pharmaceutical composition as claimed in claim 1 wherein the Benzyl benzoate used is replaced in part by 5% to 10% w/v of polyoxyethylene glycolated castor oils.

5. The composition according to claim 4 wherein the polyoxyethylene glycolated castor oils is CREMOPHOR EL.

6. A pharmaceutical composition as claimed in claim 1 further comprising an anti-oxidant.

7. A therapeutic injectable analgesic pharmaceutical composition for intra-muscular administration according to claim 1 which comprises

| Nimesulide | 2.5% to 10% w/v |
| Dimethylacetamide | 5% to 12% w/w |
| Benzyl benzoate | 20% to 50% w/v and |
| Ethyl oleate | 30% to 65% w/v. |

8. The pharmaceutical composition of claim 7 further comprising up to 10% w/v benzyl alcohol.

9. A process for the preparation of a therapeutic injectable analgesic composition containing nimesulide for intra-muscular administration which comprises:

(a) mixing 5% to 12% w/v of dimethylacetamide and 20% to 50% w/v of benzyl benzoate and adding 3% to 7% w/v of Nimesulide and stirring until completely dissolved;

(b) mixing separately up to 10% w/v of Benzyl alcohol and a portion of 30% to 65% w/v of ethyl oleate; and (c) adding the mixture obtained in step (a) to the mixture obtained in step (b) under slow stirring.

10. The process as claimed in claim 9 wherein in step (a) 10% w/v of dimethylacetamide and 40% w/v of Benzyl benzoate are mixed and to that is added 5% w/v of Nimesulide.

11. The process as claimed in claim 9 wherein in step b) 2% w/v of Benzyl alcohol and a portion of 30% to 65% w/v of ethyl oleate are mixed.

12. The process as claimed in claim 9 wherein the Benzyl benzoate used in step (a) is replaced in part by 5% to 10% w/v of polyoxyethylene glycolated castor oils.

13. The process according to claim 12 wherein the polyoxyethylene glycolated castor oils is CREMOPHOR EL.

14. The process as claimed in claim 9 further comprising adding an antioxidant.

15. A therapeutic injectable analgesic pharmaceutical composition for intra-muscular administration prepared by the process of claim 9.

16. A process for the preparation of a therapeutic injectable analgesic composition containing nimesulide for intra-muscular administration which comprises:

(a) mixing 5% to 12% w/v of Dimethylacetamide and 20% to 50% w/v of Benzyl benzoate and adding 3% to 7% w/v of Nimesulide and stirring until completely dissolved;

(b) adding 30% to 65% w/v of Ethyl oleate to the mixture obtained in step (a) under slow stirring.

* * * * *